United States Patent

Dürsch et al.

[11] 4,388,252
[45] Jun. 14, 1983

[54] PROCESS FOR THE MANUFACTURE OF VINYL PHOSPHONIC ACID DERIVATIVES

[75] Inventors: Walter Dürsch, Königstein; Hans-Jerg Kleiner, Kronberg, both of Fed. Rep. of Germany

[73] Assignee: Hoechst Aktiengesellschaft, Frankfurt, Fed. Rep. of Germany

[21] Appl. No.: 224,316

[22] Filed: Jan. 12, 1981

[30] Foreign Application Priority Data

Jan. 19, 1980 [DE] Fed. Rep. of Germany ....... 3001894

[51] Int. Cl.³ .......................... C07F 9/388; C07F 9/40
[52] U.S. Cl. .............................. 260/968; 260/502.4 P; 260/502.4 R; 260/933
[58] Field of Search ............... 260/956, 968, 933, 988, 260/502.4 R, 502.4 P

[56] References Cited

U.S. PATENT DOCUMENTS 3,062,792 11/1962 McConnell et al. ................ 260/968

OTHER PUBLICATIONS

Yamagami et al., "Nippon Kagaku Kaisha", vol. 10 (1972), pp. 1991-1993.

Wagner et al., "Synthetic Organic Chemistry", (1953), J. Wiley & Sons, New York, pp. 41-42.

Primary Examiner—Anton H. Sutto
Attorney, Agent, or Firm—Connolly and Hutz

[57] ABSTRACT

Process for the manufacture of vinyl phosphonic acid derivatives of the formula

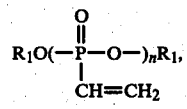

with $R_1$ being hydrogen or alkyl with 1 to 4, preferably 1 to 2, carbon atoms and n being 1 or 2, which comprises heating to 150°-270° C., preferably 170° to 230° C., 2-acetoxyethane phosphonic acid dialkyl esters of the formula

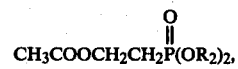

with $R_2$ being alkyl with 1 to 4, preferably 1 to 2, carbon atoms, in the presence of acidic or basic catalysts.

4 Claims, No Drawings

PROCESS FOR THE MANUFACTURE OF VINYL PHOSPHONIC ACID DERIVATIVES

As it is known, vinyl phosphonic acid derivatives can be obtained from 2-chloroethane phosphonic acid derivatives. Synthesis of these 2-chloroethane phosphonic acid derivatives, however, is technically complicated. Synthesis of 2-acetoxyethane phosphonic acid diesters from vinyl acetate and dialkyl phosphites (German Offenlegungsschift No. 2,127,821) is less complicated. Vinyl phosphonic acid dimethyl ester can be obtained in an about 50% yield from 2-acetoxy-ethane phosphonic dimethyl ester by splitting off acetic acid at 550° C. (M. Yamagami et al., Nippon Kagaku Kaisha 10, 1991 (1972)). It is an object of the invention to find an improved process for preparing vinyl phosphonic acid derivatives from 2-acetoxyethane phosphonic acid diesters.

It has surprisingly been found that vinyl phosphonic acid derivatives of the formula $$R_1O(-\underset{\underset{CH=CH_2}{|}}{\overset{\overset{O}{\|}}{P}}-O-)_nR_1,$$

with $R_1$ being hydrogen or alkyl with 1 to 4, preferably 1 to 2, carbon atoms and n being 1 or 2, can be prepared in simple and economic manner by heating to 150°–270° C., preferably 170°–230° C., 2-acetoxyethane phosphonic acid dialkyl esters of the formula $$CH_3COOCH_2CH_2\overset{\overset{O}{\|}}{P}(OR_2)_2,$$

with $R_2$ being alkyl with 1 to 4, preferably 1 to 2, carbon atoms, in the presence of acidic or basic catalysts and thus splitting off alkyl acetate of the formula $$CH_3COOR_2,$$

with $R_2$ having the abovementioned meaning.

It is surprising that vinyl phosphonic acid derivatives are even formed in a considerably lower temperature range than is known, and that not acetic acid but alkyl acetate is split off.

Suitable starting materials are, for example, 2-acetoxyethane phosphonic acid dimethyl ester, diethyl ester, diisopropyl ester and di-n-butyl ester. Especially preferred is the 2-acetoxyethane phosphonic acid dimethyl ester.

Numerous compounds can be used as acidic or basic catalysts. The following compounds may be used as acidic catalysts:
(A) Sulfuric acid or phosphoric acid.
(B) Halogen-containing carboxylic acids with a $P_{Ka}$ value <2.5 such as dichloroacetic acid, trichloroacetic acid, trifluoroacetic acid.
(C) Aromatic sulfonic acids with a $P_{Ka}$ value <2.5 such as benzenesulfonic acid, p-toluenesulfonic acid.
(D) Preferably phosphinic acids with 2 to 18 carbon atoms, such as dimethylphosphinic acid, methylethylphosphinic acid, dioctylphosphinic acid, methylphenylphosphinic acid, diphenylphosphinic acid.
(E) More preferably phosphonic acids with 1 to 18 carbon atoms and their semi-esters with 1 to 4 carbon atoms in the alcohol radical such as methanephosphonic acid, propanephosphonic acid, propanephosphonic acid monomethyl ester, octadecanephosphonic acid, 2-acetoxyethanephosphonic acid, 2-acetoxyethanephosphonic acid monomethyl ester, vinyl phosphonic acid, vinyl phosphonic acid monoethyl ester, benzenephosphonic acid.
(F) Pyrophosphonic acids or their semi-esters such as methanepyrophosphonic acid, benzenepyrophosphonic acid, vinyl pyrophosphonic acid, vinyl pyrophosphonic acid monomethyl ester are also especially preferred.
(G) The acidic reaction mixtures which are obtained during the process according to the invention are also especially suitable.

Suitable basic catalysts are:
(A) Tertiary aliphatic and aromatic amines and phosphines with 3 to 18 carbon atoms, such as trimethylamine, tripropylamine, tributylamine, triphenylamine, trimethylphosphine, triethylphosphine, tripropylphosphine, tributylphosphine, triphenylphosphine, tris-(p-dimethylaminophenyl)-phosphine and the corresponding mixed amines, phosphines, phospholanes and phospholenes, such as dimethylethylamine, diethylbutylamine, N-dimethylaniline, 4-methyl-N-dimethylaniline, N-diethylaniline, N,N-tetramethylphenyldiamine, or N-methylpyrrolidine, methyldiethylphosphine, dimethyl propylphosphine, diethyl benzylphosphine, 1-methylphospholene-3 and 1-ethyl-3-methyl-phospholene-3.
(B) Quaternary ammonium salts or phosphonium salts with 3 to 18 carbon atoms such as tetramethylammonium chloride or bromide, tetraethylphosphonium chloride, trimethylbenzylammonium chloride, triethylbenzylammonium chloride, triethylbenzylammonium bromide, trimethylbenzylphosphonium chloride, triphenylethylphosphonium-2,4-diaminobenzosulfonate.
(C) Heterocyclic compounds with aromatic character such as pyridine, quinoline, their different alkyl and dialkyl, preferably methyl or dimethyl derivatives, imidazole, N-vinyl-imidazole, benzothiazole, 2-amino-6-ethoxybenzothiazole and phosphabenzenes.
(D) Acid amides such as dimethylformamide, N-dimethylacetamide, N-diethylpropionamide, N-dimethylbenzamine, N-methyl-pyrrolidone, N,N'-tetramethylterephthalic acid diamide or ureas such as tetramethyl urea and trimethylphenyl urea.
(E) Other nitrogen or phosphorus compounds with a valence higher than 3 of a N- or P-atom such as pyridine-N-oxide, trimethylphosphine oxide, tributylphosphine oxide, trihexylphosphine oxide, triphenylphosphine oxide, dimethylphenylphosphine oxide, dimethylphenylphosphine sulfide, dimethylchloromethylphosphine oxide, dimethyleicosylphosphine oxide, dimethyldodecylphosphine oxide, dimethylphosphine oxide, dimethylpyrrolidinyl-1-methylphosphine-oxide, triphenylphosphine dichloride, dimethyldodecylphosphine sulfide, triphenylphosphinimine, dimethylchloromethylphosphine dichloride, N-2-dimethylphosphinylethylmethylacetamide, N-2-dimethylphosphinylethylmethylamine, phospholene oxides such as 1-methylphospholene-1-oxide and 1-ethyl-3-methyl-phospholene-1-oxide.
(F) Amides of phosphinous and phosphonous acid and of phosphinic and phosphonic acids as well as their thioanalogs, such as ethane phosphonic acid-bis-diethylamide, methane-butane phosphinous acid dimethylamide, diethyl phosphinous acid isobutylamide. Moreover triamides of phosphoric and thiophosphoric acid such as hexamethylphosphoric acid triamide.

The catalysts are used in amounts of 0.01 to 10, preferably from 0.1 to 5, % by weight. When using short-chain alkane phosphonic acids with up to 4 carbon atoms, their monoalkyl esters or the acidic reaction mixtures obtained, even larger amounts of 10 to 50% by weight can be employed, since the mixture of vinyl and alkane phosphonic acid derivatives obtained by this method of operation, can be interesting intermediate products per se.

The process, in general, is carried out by mixing the starting product with the catalyst and by heating to the required reaction temperature of 150° to 270° C., preferably 170° to 230° C.

Higher temperatures are possible, but do not mean any advantage. They possibly lead to an increased formation of by-products, but also of polymers.

Subsequently, the alkyl acetate, which is splitting off, is distilled together with small amounts of alkanol and dialkyl ether. Distillation is carried out under atmospheric pressure, optionally with the addition of an inert gas, such as nitrogen. In individual cases, however, it may be advantageous to distill off in vacuo. Splitting off of the alkyl acetate is terminated after 2 to about 20 hours. It can be expedient to continue stirring for 1 to 4 hours at reaction temperature. The process can also be performed continuously.

It can be advantageous to add polymerization inhibitors, such as hydroquinone, hydroquinone monomethyl ether or phenothiazine.

When 2-acetoxyethanephophonic acid diesters, which because of their preparation are contaminated with small amounts of the corresponding monoester, are used as starting products, further addition of a catalyst is not necessary. In this case, the reaction is advantageously started at about 250° C. When the acidic product, which, of course, also acts as catalyst for the reaction, has been formed in sufficient amount, the process can be continued at lower temperatures, for example at 180° to 220° C.

Essentially, the reaction product consists of a mixture of vinyl phosphonic acid dialkyl ester and vinyl phosphonic acid monoalkyl ester, vinyl phosphonic acid, vinyl pyrophosphonic acid dialkyl ester and vinyl pyrophosphonic acid monoalkyl ester and vinyl pyrophosphonic acid. Further derivatives of vinyl phosphonic acid, oligomeric pyrophosphonic acids, can possibly also be present. For practice, an isolation of the individual components from the mixture is not necessary and, therefore, the reaction mixture can directly be used for preparation of flameproofing products. Moreover, it can be used according to the process of German Offenlegungsschrift No. 2,129,584 for preparing vinylethane phosphonic acid dichloride and/or 2-chloroethane phosphonic acid dichloride. For isolating the individual components in pure form from the reaction mixture obtained, the reaction mixture is first neutralized with alkali in a suitable solvent and the precipitated salts are separated from the diesters. The alkali metal salts of phosphonic acids or pyrophosphonic acids can be separated from the salts of phosphonic acid monoesters or pyrophosphonic acid monoesters by means of fractionated crystallization.

The following examples illustrate the invention.

EXAMPLE 1

200 g of 2-acetoxyethane phosphinic acid dimethyl ester and 1 g of 4-dimethylaminopyridine are heated to 225°–230° C. while stirring. 74 g of methyl acetate (98% of the theory) are distilled off over a column over a period of 2 hours. In a cooling trap, subsequent to the apparatus, 7 g of low boiling products are collected. Stirring is continued for 1 hour at reaction temperature. 118 g of a reaction product are obtained which, as proved by the $^1$H-NMR spectrum, contains about 85% of vinyl phosphonic acid derivatives.

EXAMPLE 2

200 g of 2-acetoxyethane phosphonic acid dimethyl ester and 10 g of triphenyl phosphine are heated to 210°–225° C. while stirring. During 3.5 hours, 71 g of methyl acetate (94% of the theory) are distilled off. Stirring is continued for 1 hour at reaction temperature. 124 g of a reaction product are obtained which contains 70% of vinyl phosphonic acid derivatives.

EXAMPLE 3

300 g of 2-acetoxyethane phosphonic acid dimethyl ester which, as a result of their preparation, contain 1 g of 2-acetoxyethane phosphonic acid monomethyl ester, are heated while stirring for 1 hour to 246° C. and subsequently for 3 hours to 220°–230° C. 108 g of methyl acetate which contain 2.4% of methanol and 2.5% of dimethyl ether are distilled over a column. In a cooling trap subsequent to the apparatus, 6.5 g of methyl acetate and 3 g of dimethyl ether are collected. Stirring is continued for 1 hour at 210°–230° C. Again 6 g of low boiling products are collected in the cooling trap subsequent to the apparatus. 170 g of a reaction mixture containing 70% of vinyl phophonic acid derivatives, are obtained.

EXAMPLE 4

300 g of 2-acetoxyethane phosphonic acid dimethyl ester and 6 g of phosphoric acid trisdimethylamide are heated while stirring to 200°–220° C. for about 7 hours with distillation of 105 g of methyl acetate over a column. 8 g of low boiling products are collected in a cooling trap subsequent to the apparatus. 182 g of a reaction mixture essentially consisting of vinyl phosphonic acid derivatives are obtained.

EXAMPLE 5

300 g of 2-acetoxyethane phosphonic acid dimethyl ester and 3 g of trimethylphosphine oxide are heated to 200°–220° C. for 8.5 hours while stirring. 93 g of methyl acetate are distilled off. 7.5 g of low boiling products are collected in a cooling trap subsequent to the apparatus. Stirring is continued for 1 hour at 215° C. 180 g of a reaction mixture are obtained containing 6% of vinyl phosphonic acid dimethyl ester, 17% of vinyl phosphonic acid monomethyl ester, 5% of vinyl phosphonic acid, 2% of vinyl pyrophosphonic acid dimethyl ester, 19% of vinyl pyrophosphonic acid monomethyl ester and 15% of vinyl pyrophosphonic acid, relative to the total amount of the phosphorus signals in the $^{31}$P-NMR spectrum.

EXAMPLE 6

300 g of 2-acetoxyethane phosphonic acid dimethyl ester and 6 g of dimethylformamide are heated to 215° C. while stirring. 104 g of methyl acetate are distilled off over a column over a period of 5 hours and 35 minutes. 7.5 g of low boiling products are collected in a cooling trap subsequent to the apparatus. There are obtained 180 g of reaction mixture containing 7% of vinyl phosphonic acid dimethyl ester, 23% of vinyl phosphonic acid monomethyl ester, 7% of vinyl phosphonic acid, 1% of vinyl pyrophosphonic acid dimethyl ester, 17% of vinyl pyrophosphonic acid monomethyl ester and 16% of vinyl pyrophosphonic acid, relative to the total amount of the phosphorus signals in the $^{31}$P-NMR spectrum.

EXAMPLE 7

200 g of 2-acetoxyethane phosphonic acid diethyl ester and 7 g of triphenylphosphine are heated to 200°–235° C. for 3 hours while stirring. 79 g of ethyl acetate are distilled off over a column. 4 g of low boiling products are collected in a cooling trap subsequent to the apparatus. 109 g of a reaction mixture are obtained, containing 23% of vinyl phosphonic acid diethyl ester, 20% of vinyl phosphonic acid monoethyl ester and 23% of vinyl phosphonic acid, relative to the total amount of the phosphorus signals in the $^{31}$P-NMR spectrum. The portions of pyrophosphonic acid derivatives were not determined.

EXAMPLE 8

1,180 g of 2-acetoxyethane phosphonic acid dimethyl ester and 20 g of vinyl phosphonic acid are heated under nitrogen to 210°–220° C. while stirring. Within 9 hours, 476 g of methyl acetate, which contain 1% of methanol and 4.6% of dimethyl ether, are distilled off. 33 g of low boiling products, essentially consisting of dimethyl ether are collected in a cooling trap subsequent to the apparatus. 685 g of a reaction product containing 70% of vinyl phosphonic acid derivatives, are obtained.

EXAMPLE 9

1,700 g of 2-acetoxyethane phosphonic acid dimethyl ester and 154 g of the reaction product of Example 8 are heated to 190°–195° C. for 16 hours while stirring. 687 g of methyl acetate, containing 6.8% of methanol and 0.2% of dimethyl ether are distilled off. 35 g of low boiling products are collected in a cooling trap subsequent to the apparatus. 1,126 g of a reaction product containing 70% of vinyl phosphonic acid derivatives are obtained.

EXAMPLE 10

784.4 g of 2-acetoxyethane phosphonic acid dimethyl ester and 214 g of the reaction product of Example 9 are heated to 190°–195° C. for 10 hours while stirring, whereby 296 g of methyl acetate, containing 3.4% of methanol and 0.2% of dimethyl ether are distilled off. 41 g of low boiling products are collected in a cooling trap subsequent to the apparatus. 649 g of a reaction product containing 70% of vinyl phosphonic acid derivatives, are obtained.

What is claimed is:

1. A process for the manufacture of a vinyl phosphonic acid derivative of the formula

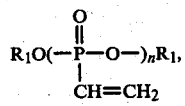

wherein $R_1$ is hydrogen of alkyl having 1 to 4 carbon atoms and n is 1 or 2, said process comprising heating to 150°–270° C. a 2-acetoxyethane phosphonic acid dialkyl ester of the formula

wherein $R_2$ is alkyl having 1 to 4 carbon atoms in the presence of a catalytic amount of an acidic or basic catalyst.

2. The process of claim 1 wherein $R_1$ is alkyl having 1 to 2 carbon atoms.

3. The process of claim 1 wherein said temperature is 170°–230° C.

4. The process of claim 1 wherein $R_2$ is alkyl having 1 to 2 carbon atoms.

* * * * *